US010398292B2

(12) United States Patent
Drach et al.

(10) Patent No.: US 10,398,292 B2
(45) Date of Patent: Sep. 3, 2019

(54) FLUID DISPENSING CONTROL SYSTEMS AND METHODS

(71) Applicant: Floshield, Inc., Cupertino, CA (US)

(72) Inventors: Gregory P. Drach, Liberty Township, OH (US); Wayne L. Poll, New Albany, OH (US)

(73) Assignee: Floshield, Inc., Cupertino, CA (US)

( * ) Notice: Subject to any disclaimer, the term of this patent is extended or adjusted under 35 U.S.C. 154(b) by 0 days.

(21) Appl. No.: 14/767,862

(22) PCT Filed: Mar. 13, 2014

(86) PCT No.: PCT/US2014/026511
§ 371 (c)(1),
(2) Date: Aug. 13, 2015

(87) PCT Pub. No.: WO2014/151824
PCT Pub. Date: Sep. 25, 2014

(65) Prior Publication Data
US 2015/0374212 A1 Dec. 31, 2015

Related U.S. Application Data

(60) Provisional application No. 61/783,847, filed on Mar. 14, 2013.

(51) Int. Cl.
*A61B 1/015* (2006.01)
*A61M 5/31* (2006.01)
(Continued)

(52) U.S. Cl.
CPC .......... *A61B 1/015* (2013.01); *A61B 1/00091* (2013.01); *A61B 1/00096* (2013.01);
(Continued)

(58) Field of Classification Search
CPC ............ A61B 1/00091; A61B 1/00094; A61B 1/00112; A61B 1/00119; A61B 1/00121;
(Continued)

(56) References Cited

U.S. PATENT DOCUMENTS

| 3,373,736 | A | 3/1968 | Fiore et al. |
| D230,727 | S | 3/1974 | Richman |

(Continued)

FOREIGN PATENT DOCUMENTS

| EP | 0664101 A1 | 7/1995 |
| EP | 0790652 A1 | 8/1997 |

(Continued)

OTHER PUBLICATIONS

Poll et al.; U.S. Appl. No. 15/385,693 entitled "Devices, systems, and methods for performing endoscopic surgical procedures," filed Dec. 20, 2016.

(Continued)

Primary Examiner — Ryan N Henderson
(74) Attorney, Agent, or Firm — Shay Glenn LLP

(57) ABSTRACT

Systems and methods make use of a fluid dispensing control apparatus having a sheath, a tubing system, and a fluid source to facilitate control of fluid during intra-operative defogging, surgical debris deflection, and cleaning of a laparoscope lens during minimally invasive surgery. The sheath has at least one lumen for providing fluid to the distal end of the sheath to clean the laparoscope. At the end of the lumen is a one-way control valve to prevent the uncontrolled flow of fluid from the lumen. The apparatus may also have a syringe assembly wherein a syringe is inserted into a syringe mating mechanism having a gasket which can facilitate the immediate relief of pressure in the fluid lumen once the pressure on the syringe plunger is released.

17 Claims, 5 Drawing Sheets

(51) Int. Cl.
*A61B 1/12* (2006.01)
*A61B 1/00* (2006.01)
*A61B 1/313* (2006.01)

(52) U.S. Cl.
CPC ...... *A61B 1/00128* (2013.01); *A61B 1/00135* (2013.01); *A61B 1/12* (2013.01); *A61B 1/126* (2013.01); *A61B 1/3132* (2013.01); *A61M 5/31* (2013.01); *A61M 5/3134* (2013.01); *A61M 5/3137* (2013.01)

(58) Field of Classification Search
CPC ............ A61B 1/00128; A61B 1/00135; A61B 1/00142; A61B 1/00154; A61B 1/015; A61B 1/12; A61B 1/126; A61B 1/127; A61B 1/128; A61M 5/178; A61M 5/31; A61M 5/3134; A61M 5/3135; A61M 5/3137; A61M 5/3139
USPC ......... 604/23, 26, 43–45; 600/121–125, 132, 600/156–159, 169, 175–177
See application file for complete search history.

(56) References Cited

U.S. PATENT DOCUMENTS

| | | |
|---|---|---|
| 4,207,874 A | 6/1980 | Choy |
| 4,279,246 A | 7/1981 | Chikama |
| 4,281,646 A | 8/1981 | Kinoshita |
| 4,436,087 A * | 3/1984 | Ouchi ................ A61B 1/0008 600/106 |
| D277,408 S | 1/1985 | Kubokawa et al. |
| D277,505 S | 2/1985 | Kubokawa et al. |
| 4,497,550 A | 2/1985 | Ouchi et al. |
| 4,537,209 A | 8/1985 | Sasa |
| D280,929 S | 10/1985 | Lystager |
| 4,548,197 A | 10/1985 | Kinoshita |
| 4,552,130 A | 11/1985 | Kinoshita |
| D284,028 S | 5/1986 | Seager |
| 4,598,698 A | 7/1986 | Siegmund |
| 4,616,169 A | 10/1986 | Profitt |
| 4,617,013 A | 10/1986 | Betz |
| 4,633,855 A | 1/1987 | Baba |
| 4,637,814 A | 1/1987 | Leiboff |
| 4,646,722 A | 3/1987 | Silverstein et al. |
| 4,735,603 A | 4/1988 | Goodson et al. |
| 4,741,326 A | 5/1988 | Sidall et al. |
| 4,748,970 A | 6/1988 | Nakajima |
| 4,760,838 A | 8/1988 | Fukuda |
| 4,773,413 A | 9/1988 | Hussein et al. |
| 4,794,911 A | 1/1989 | Okada |
| 4,800,869 A | 1/1989 | Nakajima |
| 4,877,016 A | 10/1989 | Kantor et al. |
| 4,941,872 A | 7/1990 | Felix et al. |
| 4,973,321 A | 11/1990 | Michelson |
| 4,991,565 A | 2/1991 | Takahashi et al. |
| 4,998,527 A | 3/1991 | Meyer |
| 5,009,655 A | 4/1991 | Daignault, Jr. et al. |
| 5,019,054 A | 5/1991 | Clement et al. |
| 5,027,791 A | 7/1991 | Takahashi |
| 5,050,585 A | 9/1991 | Takahashi |
| 5,133,336 A | 7/1992 | Savitt et al. |
| 5,144,942 A | 9/1992 | Decarie et al. |
| 5,147,292 A | 9/1992 | Kullas et al. |
| 5,163,927 A | 11/1992 | Woker et al. |
| 5,167,220 A | 12/1992 | Brown |
| 5,201,908 A | 4/1993 | Jones |
| 5,207,213 A | 5/1993 | Auhll et al. |
| 5,225,001 A | 7/1993 | Manni et al. |
| 5,279,549 A | 1/1994 | Ranford |
| D346,023 S | 4/1994 | Stewart, Sr. |
| 5,306,272 A | 4/1994 | Cohen et al. |
| 5,312,400 A | 5/1994 | Bales et al. |
| 5,313,934 A | 5/1994 | Wiita et al. |
| 5,320,091 A | 6/1994 | Grossi et al. |
| 5,322,070 A | 6/1994 | Goodman et al. |
| 5,328,458 A | 7/1994 | Sekino et al. |
| 5,336,170 A | 8/1994 | Salerno et al. |
| 5,339,800 A | 8/1994 | Wiita et al. |
| 5,359,991 A | 11/1994 | Takahashi et al. |
| 5,364,407 A | 11/1994 | Poll |
| 5,386,817 A | 2/1995 | Jones |
| 5,392,766 A | 2/1995 | Masterson et al. |
| 5,400,767 A | 3/1995 | Murdoch |
| 5,448,891 A | 9/1995 | Nakagiri et al. |
| 5,448,990 A | 9/1995 | De Faria Correa |
| 5,464,008 A | 11/1995 | Kim |
| 5,468,240 A | 11/1995 | Gentelia et al. |
| D369,862 S | 5/1996 | Stewart, Jr. |
| 5,514,074 A | 5/1996 | Yabe et al. |
| 5,514,084 A | 5/1996 | Fisher |
| 5,518,502 A | 5/1996 | Kaplan et al. |
| 5,562,600 A | 10/1996 | Matsuno |
| 5,563,737 A | 10/1996 | Kamrat |
| 5,569,157 A | 10/1996 | Nakazawa et al. |
| 5,575,753 A | 11/1996 | Yabe et al. |
| 5,575,756 A | 11/1996 | Karasawa et al. |
| 5,605,532 A | 2/1997 | Schermerhorn |
| 5,630,795 A | 5/1997 | Kuramoto et al. |
| 5,637,075 A | 6/1997 | Kikawada |
| 5,647,840 A | 7/1997 | D'Amelio et al. |
| 5,697,888 A | 12/1997 | Kobayashi et al. |
| 5,722,933 A * | 3/1998 | Yabe ..................... A61B 1/012 600/121 |
| 5,746,695 A | 5/1998 | Yasui et al. |
| 5,788,628 A | 8/1998 | Matsuno et al. |
| 5,857,961 A | 1/1999 | Vanden Hoek et al. |
| 5,863,286 A | 1/1999 | Yabe et al. |
| 5,865,730 A | 2/1999 | Fox et al. |
| 5,868,663 A | 2/1999 | Katsurada et al. |
| 5,869,107 A | 2/1999 | Shimizu et al. |
| 5,894,369 A | 4/1999 | Akiba et al. |
| 5,922,105 A | 7/1999 | Fujii et al. |
| 5,954,637 A | 9/1999 | Francis |
| 5,957,888 A | 9/1999 | Hinchliffe |
| 5,989,183 A | 11/1999 | Reisdorf et al. |
| 6,017,333 A | 1/2000 | Bailey |
| 6,040,053 A | 3/2000 | Scholz et al. |
| 6,071,606 A | 6/2000 | Yamazaki et al. |
| D428,487 S | 7/2000 | Renner et al. |
| 6,096,026 A | 8/2000 | Schultz |
| 6,110,103 A | 8/2000 | Donofrio |
| 6,110,259 A | 8/2000 | Schultz et al. |
| 6,113,586 A | 9/2000 | Ouchi |
| 6,117,070 A * | 9/2000 | Akiba ................. A61B 1/00137 600/154 |
| 6,126,592 A | 10/2000 | Proch et al. |
| 6,149,659 A | 11/2000 | Ahmed |
| 6,156,409 A | 12/2000 | Doushita et al. |
| 6,176,825 B1 | 1/2001 | Chin et al. |
| 6,206,825 B1 | 3/2001 | Tsuyuki |
| 6,234,635 B1 | 5/2001 | Seitzinger et al. |
| 6,282,442 B1 | 8/2001 | DeStefano et al. |
| 6,293,909 B1 | 9/2001 | Chu et al. |
| 6,299,592 B1 | 10/2001 | Zander |
| 6,306,932 B1 | 10/2001 | Yamamoto et al. |
| 6,309,347 B1 | 10/2001 | Takahashi et al. |
| 6,354,992 B1 | 3/2002 | Kato |
| 6,361,492 B1 | 3/2002 | Santilli |
| 6,383,134 B1 | 5/2002 | Santilli |
| 6,409,657 B1 | 6/2002 | Kawano |
| 6,425,535 B1 | 7/2002 | Akiba |
| 6,447,446 B1 | 9/2002 | Smith et al. |
| 6,582,357 B2 | 6/2003 | Ouchi et al. |
| 6,589,316 B1 | 7/2003 | Schultz et al. |
| D481,126 S | 10/2003 | Hayamizu |
| 6,645,197 B2 | 11/2003 | Garrison et al. |
| D484,594 S | 12/2003 | Hayamizu |
| D486,910 S | 2/2004 | Hayamizu et al. |
| 6,695,772 B1 | 2/2004 | Bon et al. |
| 6,699,185 B2 | 3/2004 | Gminder et al. |
| 6,712,479 B1 | 3/2004 | Seitzinger et al. |
| 6,712,757 B2 | 3/2004 | Becker et al. |
| 6,712,759 B2 | 3/2004 | Muller |

(56) References Cited

U.S. PATENT DOCUMENTS

| | | |
|---|---|---|
| 6,752,755 B2 | 6/2004 | Akiba |
| 6,755,782 B2 | 6/2004 | Ogawa |
| D493,529 S | 7/2004 | Hayamizu et al. |
| 6,764,445 B2 | 7/2004 | Ramans et al. |
| 6,780,516 B2 | 8/2004 | Chen |
| 6,783,845 B2 | 8/2004 | Zhang et al. |
| D498,846 S | 11/2004 | Hayamizu et al. |
| 6,814,697 B2 | 11/2004 | Ouchi |
| 6,857,436 B2 | 2/2005 | Labib et al. |
| 6,858,005 B2 | 2/2005 | Ohline et al. |
| 6,882,236 B2 | 4/2005 | Dinn et al. |
| 6,889,400 B2 | 5/2005 | Kawazoe et al. |
| 6,921,362 B2 | 7/2005 | Ouchi |
| 6,921,380 B1 | 7/2005 | Epstein et al. |
| 6,977,053 B2 | 12/2005 | Mukasa et al. |
| 6,984,204 B2 | 1/2006 | Akiba |
| 6,989,183 B2 | 1/2006 | McKillip |
| 7,074,180 B2 | 7/2006 | Bertolero et al. |
| 7,080,641 B2 | 7/2006 | Gomez |
| 7,087,013 B2 | 8/2006 | Belson et al. |
| 7,150,713 B2 | 12/2006 | Shener et al. |
| D534,655 S | 1/2007 | Iranyi et al. |
| D535,743 S | 1/2007 | Williams |
| 7,169,167 B2 | 1/2007 | Chu |
| 7,198,599 B2 | 4/2007 | Goto et al. |
| 7,223,231 B2 | 5/2007 | Akiba |
| 7,250,028 B2 | 7/2007 | Julian et al. |
| 7,270,670 B1 | 9/2007 | Yencho |
| 7,341,556 B2 | 3/2008 | Shalman |
| D573,711 S | 7/2008 | Johnson et al. |
| 7,413,543 B2 | 8/2008 | Banik et al. |
| 7,435,218 B2 | 10/2008 | Krattiger et al. |
| D600,807 S | 9/2009 | Dienst et al. |
| D613,403 S | 4/2010 | Poll et al. |
| 7,803,109 B2 | 9/2010 | Gomez |
| 7,803,144 B1 | 9/2010 | Vollrath |
| 7,927,271 B2 | 4/2011 | Dimitriou et al. |
| 8,047,215 B1 | 11/2011 | Sasaki |
| 8,062,214 B2 | 11/2011 | Shener et al. |
| 8,075,481 B2 | 12/2011 | Park et al. |
| 8,096,944 B2 | 1/2012 | Harrel |
| 8,226,549 B2 | 7/2012 | Kumar et al. |
| 8,419,624 B2 | 4/2013 | James et al. |
| 8,517,921 B2 | 8/2013 | Tremaglio et al. |
| 8,545,395 B2 | 10/2013 | Akahoshi et al. |
| 8,888,689 B2 | 11/2014 | Poll et al. |
| 9,050,036 B2 | 6/2015 | Poll et al. |
| 9,050,037 B2 | 6/2015 | Poll et al. |
| 9,078,562 B2 | 7/2015 | Poll et al. |
| 2001/0011162 A1 | 8/2001 | Epstein |
| 2002/0022762 A1 | 2/2002 | Beane et al. |
| 2002/0058858 A1 | 5/2002 | Ogura et al. |
| 2002/0072652 A1 | 6/2002 | Berci et al. |
| 2002/0091304 A1 | 7/2002 | Ogura et al. |
| 2002/0193806 A1 | 12/2002 | Moenning et al. |
| 2003/0200738 A1 | 10/2003 | Booth |
| 2004/0034339 A1 | 2/2004 | Stoller et al. |
| 2004/0059363 A1 | 3/2004 | Alvarez et al. |
| 2004/0082915 A1 | 4/2004 | Kadan |
| 2004/0204671 A1 | 10/2004 | Stubbs et al. |
| 2004/0216468 A1 | 11/2004 | Hatcher |
| 2005/0043683 A1 | 2/2005 | Ravo |
| 2005/0059981 A1 | 3/2005 | Poll |
| 2005/0065405 A1 | 3/2005 | Hasegawa |
| 2005/0080342 A1 | 4/2005 | Gilreath et al. |
| 2005/0113797 A1 | 5/2005 | Ott et al. |
| 2005/0119528 A1 | 6/2005 | Weinberg |
| 2005/0137529 A1 | 6/2005 | Mantell |
| 2005/0154355 A1 | 7/2005 | Gross et al. |
| 2005/0159765 A1 | 7/2005 | Moutafis et al. |
| 2005/0171467 A1 | 8/2005 | Landman |
| 2005/0171528 A1 | 8/2005 | Sartor et al. |
| 2005/0203342 A1 | 9/2005 | Kucklick et al. |
| 2005/0234301 A1 | 10/2005 | Gomez |
| 2005/0261553 A1 | 11/2005 | Swain et al. |
| 2006/0020165 A1 | 1/2006 | Adams |
| 2006/0041186 A1 | 2/2006 | Vancaillie |
| 2006/0047184 A1 | 3/2006 | Banik et al. |
| 2006/0052661 A1 | 3/2006 | Gannot et al. |
| 2006/0069306 A1 | 3/2006 | Banik et al. |
| 2006/0252993 A1 | 11/2006 | Freed et al. |
| 2006/0270910 A1 | 11/2006 | Davis |
| 2007/0088275 A1 | 4/2007 | Stearns et al. |
| 2007/0179432 A1 | 8/2007 | Bar et al. |
| 2007/0182842 A1 | 8/2007 | Sonnenschein et al. |
| 2007/0203474 A1 | 8/2007 | Ryan et al. |
| 2007/0282253 A1 | 12/2007 | Sasaki |
| 2007/0289449 A1 | 12/2007 | Roberts et al. |
| 2007/0299310 A1 | 12/2007 | Phillips |
| 2008/0021277 A1 | 1/2008 | Stefanchik et al. |
| 2008/0051631 A1 | 2/2008 | Dejima et al. |
| 2008/0058591 A1 | 3/2008 | Saadat et al. |
| 2008/0081948 A1 | 4/2008 | Weisenburgh et al. |
| 2008/0082084 A1 | 4/2008 | Roberts et al. |
| 2008/0086704 A1 | 4/2008 | Aravamudan |
| 2008/0108871 A1 | 5/2008 | Mohr |
| 2008/0161646 A1 | 7/2008 | Gomez |
| 2008/0188715 A1 | 8/2008 | Fujimoto |
| 2008/0200765 A1 | 8/2008 | Mondschein |
| 2008/0208128 A1 | 8/2008 | Guo et al. |
| 2008/0249362 A1 | 10/2008 | Jiang et al. |
| 2008/0255419 A1 | 10/2008 | Kendale et al. |
| 2008/0255424 A1* | 10/2008 | Durgin ................ A61B 1/0008 600/156 |
| 2009/0018602 A1 | 1/2009 | Mitelberg et al. |
| 2009/0113644 A1 | 5/2009 | Heck |
| 2009/0215018 A1 | 8/2009 | Edmondson et al. |
| 2009/0234193 A1 | 9/2009 | Weisenburgh et al. |
| 2009/0253962 A1 | 10/2009 | Fernandez et al. |
| 2009/0253964 A1 | 10/2009 | Miyamoto |
| 2009/0253965 A1 | 10/2009 | Miyamoto |
| 2010/0010310 A1* | 1/2010 | Weisenburgh, II .......................... A61B 1/00091 600/156 |
| 2010/0331856 A1 | 12/2010 | Carlson et al. |
| 2012/0022331 A1 | 1/2012 | Poll et al. |
| 2012/0101337 A1 | 4/2012 | Clark et al. |
| 2012/0184897 A1 | 7/2012 | Poll |
| 2012/0197084 A1 | 8/2012 | Drach et al. |
| 2012/0310147 A1 | 12/2012 | Poll et al. |
| 2012/0316394 A1* | 12/2012 | Yoshida ............ A61B 1/00091 600/123 |
| 2013/0131580 A1 | 5/2013 | Blackhurst et al. |
| 2013/0172670 A1 | 7/2013 | Levy et al. |
| 2013/0217970 A1 | 8/2013 | Weisenburgh et al. |
| 2013/0231606 A1 | 9/2013 | Stearns et al. |
| 2013/0317295 A1 | 11/2013 | Morse |
| 2014/0069461 A1 | 3/2014 | Gomez et al. |
| 2014/0107558 A1 | 4/2014 | Gomez et al. |
| 2014/0114128 A1 | 4/2014 | Wills |
| 2014/0215736 A1 | 8/2014 | Gomez et al. |
| 2014/0371763 A1 | 12/2014 | Poll et al. |
| 2015/0005582 A1 | 1/2015 | Poll et al. |
| 2015/0038785 A1 | 2/2015 | Govrin et al. |
| 2015/0265138 A1 | 9/2015 | Poll et al. |
| 2016/0089006 A1 | 3/2016 | Poll et al. |
| 2018/0000324 A1 | 1/2018 | Poll et al. |

FOREIGN PATENT DOCUMENTS

| | | |
|---|---|---|
| EP | 1188415 A2 | 3/2002 |
| JP | 59-203534 | 11/1984 |
| JP | 61-168328 | 7/1986 |
| JP | 05-103756 A | 4/1993 |
| JP | 05-199979 | 8/1993 |
| JP | H07-275185 A | 10/1995 |
| JP | 09-135804 | 5/1997 |
| JP | 2000-225093 | 8/2000 |
| JP | 2004-267583 A | 9/2004 |
| JP | 2005-110978 | 4/2005 |
| JP | 2009-240596 A | 10/2009 |
| WO | WO92/10969 A1 | 7/1992 |
| WO | WO92/22238 A1 | 12/1992 |

(56) References Cited

FOREIGN PATENT DOCUMENTS

| | | |
|---|---|---|
| WO | WO2005/002210 A1 | 1/2005 |
| WO | WO2005/009227 A1 | 2/2005 |
| WO | WO2005/115221 A1 | 12/2005 |
| WO | WO2006/014814 A1 | 2/2006 |
| WO | WO2008/030256 A1 | 3/2008 |
| WO | WO2008/077080 A2 | 6/2008 |
| WO | WO2008/128142 A2 | 10/2008 |
| WO | WO2008/130582 A2 | 10/2008 |
| WO | WO2009/073577 A2 | 6/2009 |
| WO | WO2010/042913 A2 | 4/2010 |
| WO | WO2010/042915 A2 | 4/2010 |
| WO | WO2011/041387 A1 | 4/2011 |
| WO | WO2011/044448 A2 | 4/2011 |
| WO | WO2011/130399 A1 | 10/2011 |
| WO | WO2012/005819 A1 | 1/2012 |
| WO | WO2012/044410 A2 | 4/2012 |
| WO | WO2012/122263 A2 | 9/2012 |

OTHER PUBLICATIONS

Drach et al.; U.S. Appl. No. 14/970,296 entitled "Systems and methods for optimizing and maintaining visualization of a surgical field during the use of surgical scopes," filed Dec. 15, 2015.

Poll et al.; Design U.S. Appl. No. 29/329,224 entitled "Manifold Coupling," filed Dec. 10, 2008 (now abandoned).

Poll et al.; Design U.S. Appl. No. 29/329,225 entitled "Sheath Manifold for Maintaining Surgical Scope Visualization," filed Dec. 10, 2008 (now abandoned).

Poll et al.; Design U.S. Appl. No. 29/329,221 entitled "Handle for Maintaining Surgical Scope Visualization," filed Dec. 10, 2008 (now abandoned).

Poll et al.; Design U.S. Appl. No. 29/335,699 entitled "Surgical Scope Stabilizer," filed Apr. 20, 2009 (now abandoned).

Poll et al.; U.S. Appl. No. 14/733,752 entitled "View optimizer and stabilizer for use with surgical scopes," filed Jun. 8, 2015.

Farley et al.; Double-blind, prospective, randomized study of warmed, humidified carbon dioxide insufflation vs standard carbon dioxide for patients undergoing lararoscopic cholecystectomy; Arch Surg; 139; pp. 739-744; Jul. 2004.

Hashimoto et al.; Development of a fogless scope and its analysis using infrared radiation pyrometer; Surg Endosc; 11(8); pp. 805-808; Aug. 1997.

Lawrentschuk et al.; Laparoscopic lens fogging: A review of etiology and methods to maintain a clear visual field; Journal of Endourology; 24(6); pp. 905-913; Jun. 2010.

Ohdaira et al.; Antifogging effects of a socket-type device with the superhydrophilic, titanium dioxide coated glass for laparoscope; Surg endosc; 21(2); pp. 333-338; Dec. 2007.

Ott, Douglas E.; Chapter 1. Pneumoperitoneum: Production, management, effects and consequences; in Prevention & Management of Laparoendoscopic Surgical Complications, 1st Ed.; 6 pgs.; Jan. 1999 (retrieved from: http://laparoscopy.blogs.com/prevention_management/2006/02/chapter_1_pneum.html on Oct. 7, 2013).

Stern; Landmark strides in laparoscopic technologies: Video to robotics; General Surgery News; 40; Oct. 2013 (retrieved from http://www.generalsurgerynews.com/ViewArticle.aspx?d=In+the+News&_id=69&i=October+2013&i_jd=999&a_id=24140 on Jun. 6, 2014).

Olympus Medical Systems Corp.; Lens Cleaning Sheath (product brochure); R0153E2; 2 pgs.; Jan. 2014.

Poll et al.; U.S. Appl. No. 15/566,503 entitled "Endoscope having integrated visual field enhancement system," filed Oct. 13, 2017.

* cited by examiner

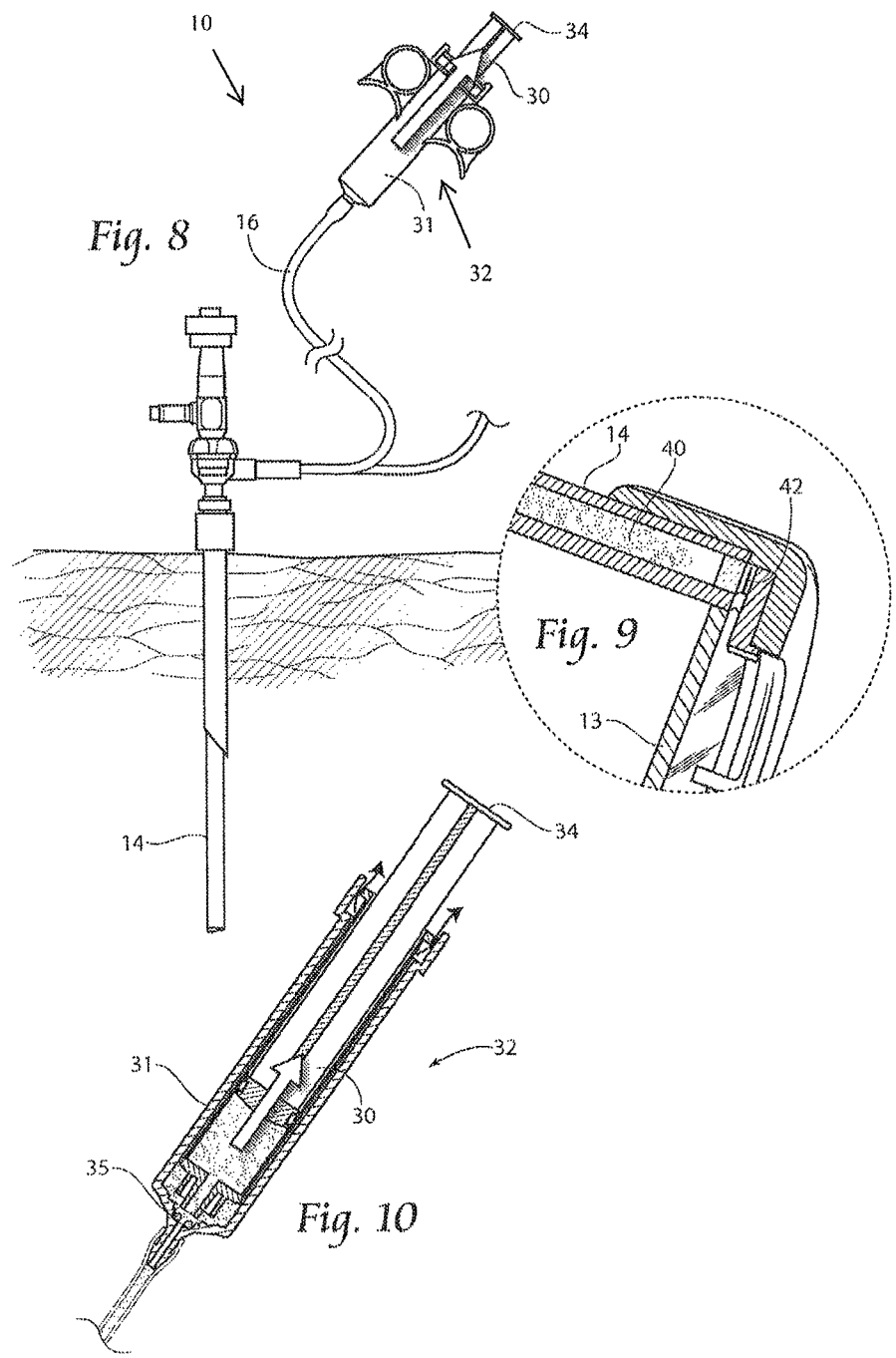

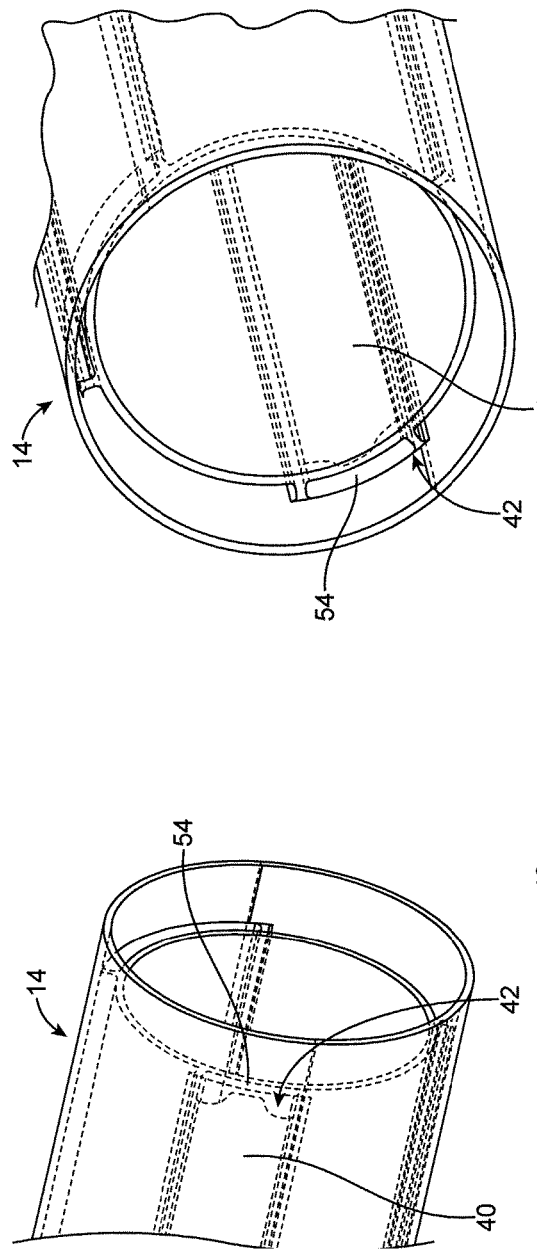
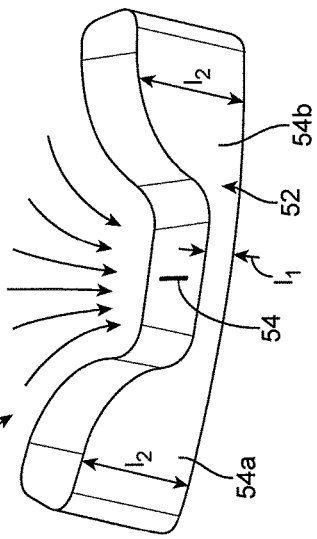
FIG. 11B
FIG. 11C
FIG. 11A

FLUID DISPENSING CONTROL SYSTEMS AND METHODS

CROSS REFERENCE TO RELATED APPLICATIONS

This application claims priority to U.S. Provisional Application No. 61/783,847, titled "Fluid Dispensing Control," and filed Mar. 14, 2013, the entirety of which is incorporated by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The invention generally relates to an apparatus for controlling the dispensing of fluids, and in particular, a dispensing control for fluid being provided to a distal end of a surgical scope, such as, a laparoscope, in order to maintain and improve visualization.

BACKGROUND

Minimally invasive surgical procedures utilizing surgical scopes are desirable because they often provide one or more of the following advantages: reduced blood loss, reduced post-operative patient discomfort, shortened recovery and hospitalization time, smaller incisions, and reduced exposure of internal organs to possible contaminants.

Generally, minimally invasive surgeries utilize scopes, such as laparoscopes, that permit remote visualization of a surgical site within a patient's body while the surgical procedure is being performed. During a laparoscopic procedure, the patient's abdominal or pelvic cavity is accessed through two or more relatively small incisions rather than through a single large incision that is typical in a conventional surgery. Surgical scopes, such as laparoscopes, usually consist in part of a rigid or relatively rigid rod or shaft having an objective lens at one end and an eyepiece and/or integrated visual display at the other. The scope may also be connected to a remote visual display device or a video camera to record surgical procedures.

In laparoscopic surgeries, the abdomen is typically inflated with a gas through the use of an insufflator, to distend the abdominal space by elevating the abdominal wall above the internal organs and thereby create a sufficient working and viewing space for the surgeon. Carbon dioxide is usually used for insufflation, though other suitable gases may also be used. Conventional insufflators are adapted to cycle on and off to maintain a preset and suitable pressure within the patient's body cavity.

The local environment within a patient's abdominal space is generally rather warm and humid, and the use of devices such as harmonic scalpels and other cutting and coagulating devices generate mist, smoke, and other debris that is released into the surgical field and often becomes suspended throughout the expanded abdominal space. Additionally, blood, bodily fluids, pieces of tissue, fat or other bodily material may come in contact with or even attach to the lens. As a result of these conditions, visualization through the scope can be significantly diminished. Typically, the only solution to fogging and debris collection on the lens is removal of the scope from the body cavity and defogging or cleaning the lens by wiping it with a cloth, warming the scope tip, or utilizing another defogging method. The need to remove the scope to defog and remove debris from the lens is inconvenient for the scope operator and the surgeon and can interrupt and undesirably prolong surgical procedures.

As such, some devices have been developed to assist in the improvement of visualization. These devices may provide gas or liquid fluids to the distal end in order to clear the lens area. The cleaning of a laparoscopic lens during a medical procedure, however, requires the ability to control the volume and placement of the fluid. Unplanned and uncontrolled releases of fluid during the procedure, usually small droplets that form drips, are a major visual distraction to the user because they can distort the image either by sliding over the lens or by forming bubbles over the lens.

One approach to preventing drips is to remove the fluid and dry the conduit by pressurized gas or by applying a vacuum to retract fluid from the conduit. In doing so, however, all the fluid must be removed from the conduit. This is difficult to accomplish at a high level of reliability because of fluid surface tension and the high positive pressure or low negative pressure required to absolutely evacuate the conduit.

As such, there remains a need for fluid dispensing control mechanism for cleaning the lens of a laparoscope in situ that prevents the uncontrolled dispensing of the fluid.

SUMMARY OF THE DISCLOSURE

The present disclosure is directed towards a view optimizing assembly for use with a laparoscope that facilitates intra-operative defogging, surgical debris deflection, and cleaning of a laparoscope lens during minimally invasive surgery, and furthermore, controls the dispensing of fluid from the device. The fluid control mechanism is directed towards a one-way valve mechanism and may further include syringe system to release fluid pressure in the fluid passageway.

In general, in one embodiment, a view optimizing assembly for use in combination with a laparoscope includes a sheath configured to be mounted over a shaft of a laparoscope. The sheath includes at least one lumen extending within a wall of the sheath from a proximal end of the sheath to a distal end of the sheath, and the at least one lumen is configured to hold a fluid therein. The sheath further includes a valve at a distal end of the at least one lumen. The valve is configured to prevent release of fluid from the at least one lumen when closed and to allow the release of fluid from the at least one lumen when open.

This and other embodiments can include one or more of the following features. The valve can be an elastomeric valve. The valve can be configured to open to allow the release of fluid when a predetermined minimum pressure is placed on the valve by the fluid within the at least one lumen. The predetermined minimum pressure can be approximately 20 mmHg. The valve can be configured to close when a pressure below a predetermined maximum pressure is placed on the valve by the fluid. The predetermined maximum pressure can be approximately 15 mmHg. The view optimizing assembly can further include a syringe mating mechanism fluidically connected to the at least one lumen. The syringe mating mechanism can include a gasket at a distal end thereof and can be configured such that, when a syringe is placed within the syringe mating mechanism and a predetermined pressure or given user pressure is placed on a plunger of the syringe, a distal end of the syringe seats within the gasket to allow fluid to flow into the at least one lumen. When the predetermined pressure or given user pressure is released from the plunger of the syringe, the gasket can be configured to act as a spring to push the syringe proximally. Removing pressure from a plunger of the syringe can immediately cause the valve to close. The gasket can be configured to seal the syringe within the syringe mating mechanism when the distal end of the syringe seats within the gasket. The gasket can be an elastomeric gasket. At least one additional lumen of the plurality of lumens can be configured to convey gas from the proximal end of the sheath to the distal end of the sheath. The valve can be a one-way valve.

In general, in one embodiment, a method of clearing debris from the lens of a laparoscope during a laparoscopic procedure includes: (1) passing fluid through a lumen of a sheath mounted over a shaft of a laparoscope; and (2) opening a valve to allow the fluid to flow over a lens of the laparoscope when a pressure in the lumen has reached a predetermined minimum amount.

This and other embodiments can include one or more of the following features. The predetermined minimum pressure can be approximately 20 mmHg. The method can further include closing the valve when a pressure in the lumen goes below a predetermined maximum pressure. The predetermined maximum pressure can be approximately 15 mmHg. Passing fluid can include ejecting fluid from a syringe into the lumen. The method can further include seating the syringe in a syringe mating mechanism to allow for the ejection of fluid. Seating the syringe in a syringe mating mechanism can include sealing the syringe against the syringe mating mechanism. Fluid from the syringe can pass into the lumen when the syringe is sealed in the syringe mating mechanism. The method can further include removing pressure from the plunger to stop the ejection of fluid and immediately cause the valve to close. The method can further include passing gas through an additional lumen of the sheath to allow the gas to flow over the lens of the laparoscope. The fluid can be a surfactant cleaning fluid, and allowing the fluid to flow over the lens can clean the lens.

In general, in one embodiment, a view optimizing assembly for use in combination with a laparoscope includes a sheath configured to be mounted over shaft of a laparoscope. The sheath includes a lumen extending from a proximal end of the sheath to a distal end of the sheath. The lumen is configured to hold a fluid therein, and a syringe mating mechanism is fluidically connected to the lumen. The syringe mating mechanism includes a gasket at a distal end thereof such that, when a syringe is placed within the dispenser and a predetermined pressure or given user pressure is placed on a plunger of the syringe, a distal end of the syringe seats within the gasket to allow fluid to flow into the lumen.

This and other embodiments can include one or more of the following features. When the predetermined pressure or given user pressure is released from the plunger of the syringe, the gasket can be configured to act as a spring to push the syringe proximally. The gasket can be configured to seal the syringe within the syringe mating mechanism when the distal end of the syringe seats within the gasket. The gasket can be an elastomeric gasket.

In general, in one embodiment, a method of clearing debris from the lens of a laparoscope during a laparoscopic procedure includes: (1) applying pressure to a fluid within a lumen of a sheath mounted over a shaft of a laparoscope; (2) opening a valve positioned in the lumen when the pressure in the lumen has reached a predetermined level; (3) stopping the applying pressure step and relieving the pressure on the fluid in the lumen; (4) venting a fluid column in communication with the fluid to atmospheric pressure; and (5) closing the valve when the relieving step has reduced the pressure in the conduit below a predetermined level.

In general, in one embodiment, a view optimizing assembly for use in combination with a laparoscope includes a sheath configured to be mounted over shaft of a laparoscope. The sheath includes a lumen extending from a proximal end of the sheath to a distal end of the sheath, and the lumen is configured to hold a fluid therein. A syringe mating mechanism is fluidically connected with the lumen through a distal opening and includes a gasket therein. A syringe includes a syringe barrel and a plunger, and the syringe barrel is configured to fit within the syringe mating mechanism. The gasket is configured to sit between the distal end of the syringe the distal opening such that, when the syringe is placed within the syringe mating mechanism, there remains some relative movement of the syringe relative to the syringe mating mechanism until a predetermined pressure or given user pressure is placed on the plunger such that the distal end of the syringe seats against the gasket, forming a fluid channel with the lumen.

Any of these embodiments can include one or more of the following features. The valve can be an orifice valve including a plug and an orifice. The orifice can be a slit. The orifice can be a tortuous path hole. The orifice can have a width or diameter of less than 0.02". The orifice can be substantially centered in the orifice plug. The orifice plug can include a central portion bordered by two side portions. The central portion can include the orifice and have a shorter length than the side portions. The side portions can include rounded edges configured to direct flow into the orifice. The orifice can be less than 1.6 mm long. The valve can include a material having a durometer of 10-40 shoreA. The predetermined minimum pressure can be at least 1 psi. The predetermined minimum pressure can be about 2 psi. The valve can be made of silicone or polyurethane. The fluid can be docusate sodium with a w/v of 0.05% to 0.25%. The valve can close when the pressure is less than 0 psi. The valve can be a duckbill, poppet, umbrella, or flap valve. The syringe dispenser can be transparent or translucent. The syringe dispenser can include grooves an inner diameter thereof running from the gasket to a proximal end of the syringe. Seating the syringe in the syringe mating mechanism can cause the predetermined minimum pressure to be applied immediately. The valve can be at the distal-most end of the lumen. The method can further include introducing relative motion between the syringe and the syringe mating mechanism to cause the fluid to pass through the valve. The relative motion can set the distal end of the syringe into sealing relation with an outlet of the syringe mechanism. Releasing pressure applied to a plunger of the syringe can permit relative motion between the syringe and the syringe mating mechanism.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 8 depicts the releasing of pressure on the syringe plunger to end the flow of fluid.

FIG. 9 is a partial cross-sectional view of a sheath of a fluid dispensing control assembly when no liquid fluid or gas is being delivered through the sheath.

FIG. 10 depicts a syringe mating mechanism when pressure has been removed from the syringe plunger.

FIGS. 11A-B show a sheath having an exemplary one-way valve at a distal end thereof. FIG. 11C is a close-up of the valve of FIGS. 11A-B.

DETAILED DESCRIPTION

Described herein is a laparoscopic sheath including a lumen for cleaning fluid and a valve configured to control the release of fluid from the lumen. The valve can advantageously retain the fluid in the lumen until sufficient pressure is applied to open the valve and dispense the fluid. The valve can be at the distal end of the lumen and can be configured to self-close when the dispensing pressure is relieved. Also described herein is a fluid delivery system configured to transfer fluid from a user-actuated syringe to the distal end of a surgical instrument, such as a laparoscope. The fluid delivery system can include a line-pressure relief system that, in conjunction with the valve, prevents secondary drips of fluid from leaving the lumen and, for example, depositing on the lens of a laparoscope.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
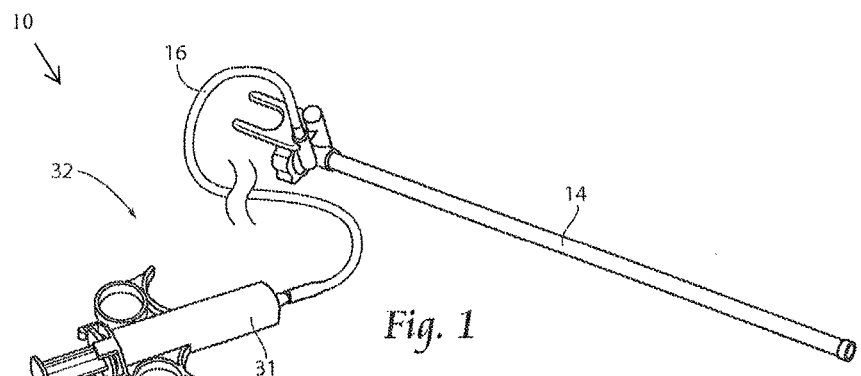
FIG. 1 is a schematic view of a fluid dispensing control assembly as described herein.

FIG. 1 shows a fluid dispensing control assembly 10 for use in association with a laparoscope. The fluid dispensing control assembly 10 includes a sheath 14 having at least one fluid lumen 40 (see FIG. 2), a fluid source 32, and at least one fluid delivery tube 16 configured to connect the lumen 40 of the sheath 14 to the fluid source 32. The components of the fluid dispensing control assembly 10 may be made from plastic materials (extruded and/or molded), metal, a composite material, or combinations thereof.

The sheath 14 is designed so that it can be mounted over the shaft of a laparoscope used during a minimally invasive surgical procedure. The sheath 14 generally comprises a shaft for receiving the laparoscope. The shaft of the sheath 14 can be sized and configured to match the size and configuration of the corresponding laparoscope. The laparoscope, and thus the distal end of the sheath 14, may have a blunt tip end or an angled tip end. The sheath 14 is preferably sized and configured to not interfere with the normal use, set-up, and features of the laparoscope in the operating room.

Figure 2:
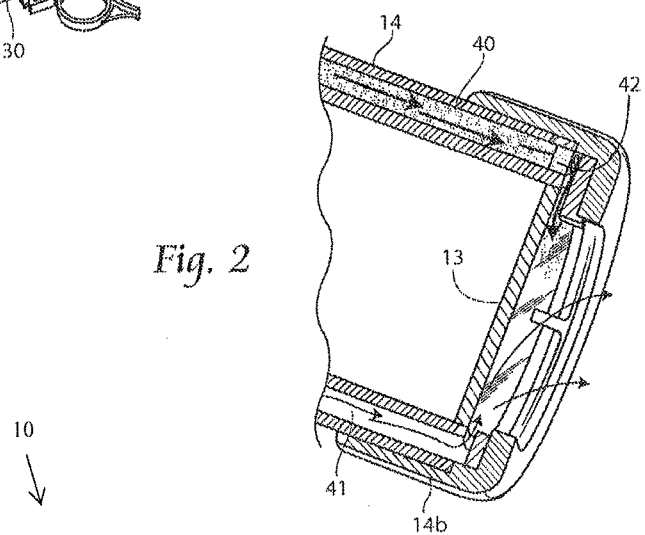
FIG. 2 is a cross-sectional view of the distal end of a sheath of a fluid dispensing control assembly.

As shown in FIG. 2, sheath 14 may have at least one lumen 40 formed within the wall of the sheath 14. The lumen 40 can have a curvilinear, oblong, or optical perimeter or cross-section. In use, the lumen 40 may be used to convey fluid to the laparoscope lens 13 at or near the distal end 14b of the sheath 14. In some embodiments, the lumen 40 may also vent or exhaust air from the distal end 14b of the sheath 14. In some embodiments, a proximal end of the lumen 40 can be open to the atmosphere. FIG. 2 also shows that the sheath 14 may have one or more additional lumens, such as gas lumen 41 that delivers gas to the distal end 14b of the sheath 14. The gas and the fluid delivered to and out from the distal end 14b of the sheath 14 may be used to clear dust and debris from the laparoscope lens 13.

Figure 3:
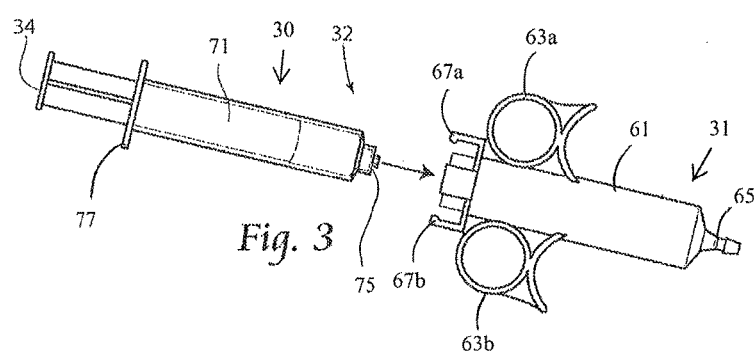
FIG. 3 is a side view of a syringe and syringe mating mechanism of FIG. 1.

Referring to FIG. 3, the fluid source 32 includes a syringe 30 and a syringe mating mechanism 31. The syringe 30 is configured to hold a fluid for delivery through the lumen 40 of the sheath 14. The fluid can be, for example, a cleaning fluid. In one embodiment, the fluid has a density of 800-1,200 kg/m$^3$, such as approximately 1,000 kg/m$^3$ (e.g., has a density similar to the density water). In one embodiment, the fluid has a viscosity of 0.6-0.9 mPas at room or body temperature (e.g., has a viscosity similar to the viscosity of water). In one exemplary embodiment, the fluid is a surfactant, such as docusate sodium with 0.05% to 0.25% w/v. Further, the syringe mating mechanism 31 is configured to mate with the syringe 30 to allow for delivery of the fluid from the syringe into the lumen 40 of the sheath 14, as described further below.

The delivery tube 16 can connect the fluid source 32 to the sheath 40 to allow fluid to be delivered from the syringe 30 to the sheath 14. The delivery tube 16 can be made, for example, of a flexible medical grade tubing. Other tubes may be provided for the delivery or removal of gas to/from the sheath 14 or removal of fluid from the sheath 14.

As shown in FIG. 2, the fluid dispensing control assembly 10 can further include a control valve 42, such as an elastomeric one-way control valve, at the distal end of the lumen 40 in the sheath 14 (and positioned near the lens 13 of the laparoscope when the sheath 14 is placed over a laparoscope). The control valve 42 can both prevent the uncontrolled release of fluid from the lumen 40 over the laparoscopic lens 13 and prevent back-flow of fluid into the lumen 40.

The valve 42 can be made of a flexible material, such as a material having a hardness of between 10 and 40 shoreA. Further, the valve 42 can be shaped so as to conform to the inner dimensions of the distal end of the lumen 40. The valve 42 can be made of a gamma stable materials, such as silicone or polyurethane, and can have adhesive properties that allow it to bond to a substrate up to pressures of 80 psi. Further, the valve 42 can be configured to self-open when a predetermined minimum pressure is applied and to self-close when a predetermined maximum pressure is applied. In some embodiment, the predetermined minimum pressure is at least 1 psi, such as at least 2 psi, while the predetermined maximum pressure is less than or equal to 0 psi. In other embodiments, the predetermined minimum pressure is 20 mmHg while the predetermined maximum pressure is 15 mmHg.

Referring to FIGS. 11A-11C, in some embodiments, the control valve 42 can be an orifice valve including a plug 52 with an orifice 54 therein. The plug 52 can be configured to seal within the distal end of the lumen 40. The plug 52 can include two curved side portions 54a,b configured to border the side walls of the lumen 40 and a central portion 58 configured to sit substantially in the center of the lumen 40. The central portion 58 can have a shorter length $l_1$ than the lengths $l_2$ of the curved portions 54a,b. In some embodiments, the shape of the plug 52 can thus look like the letter "B." The orifice 54 can sit within the central portion 58, e.g. can be substantially centered within the central portion 58 (and within the entire plug 52). Further, the curved edges of the side portions 54a,b can help direct flow from the lumen 40 towards the orifice 54, as shown by the arrows in FIG. 11C. The orifice 54 can be a slit or a tortuous path hole. Further, the orifice 54 can have a width or diameter of less than 0.02 inches and a length ($l_1$) of less than 1.6 mm. In other embodiments, the control valve 42 can be a duckbill valve, a poppet valve, an umbrella valve, or a flap valve.

Referring to FIG. 3, the syringe mating mechanism 31 can include a barrel 61 configured to hold the barrel 71 of the syringe 30. The barrel 71 of the syringe 30 can be configured to slide inside the barrel 61 of the syringe mating mechanism 31. Further, the barrel 61 of the syringe mating mechanism 31 can be clear so that graduation marks on the syringe barrel 61 can be seen therethrough. A pair of finger grips 63a,b can be attached to the barrel 61. The finger grips 63a,b can allow for a claw grip by the user with the fingers on the grips 63a,b and thumb on the plunger 34 of the syringe 30 when the syringe 30 is in the mating mechanism 31. The barrel 61 of the syringe mating mechanism 31 can end in a tapered distal tip 65 configured to mate with the tip 75 of the syringe 30. Further, the syringe mating mechanism 31 can include snaps 67a,b configured to hold the syringe 30 within the barrel 61. That is, the snaps 67a,b can be configured to move radially outward to fit the flange portion 77 of the syringe 30 therethrough. The snaps 67a,b can then move back radially inward to prevent the flange portion 77 (and thus the rest of the syringe 30) from moving proximally out of the syringe mating mechanism 31. The snaps 67a,b retain the syringe 30 in the syringe mating mechanism 31, but allow the syringe 30 to move axially within the mating mechanism 31.

Figure 4:
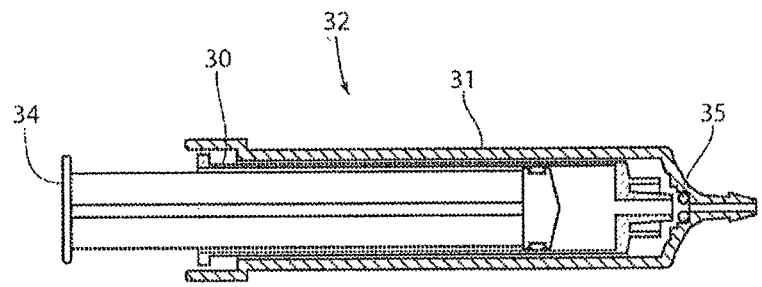
FIG. 4 is a side view of a syringe and syringe mating mechanism shown in a coupled position.

As shown in FIG. 4, the syringe mating mechanism 31 can further include an elastomeric gasket 35 (such as an o-ring or a washer) in the tapered distal tip 65. The gasket 35 can be made, for example, of silicone. The gasket 35 can be configured to form a hermetic seal between the outer diameter of the syringe 30 and the inner diameter of the syringe mating mechanism 31 when the syringe 30 is pushed fully within the syringe mating mechanism 31. In some embodiments, the barrel 61 of the syringe mating mechanism 31 can include grooves on the inner diameter extending from the gasket 35 to the proximal end of the barrel 61.

Referring to FIGS. 4-10, the syringe mating mechanism 31 is configured to allow the syringe to immediate apply pressure within the lumen 40 when the plunger 34 of the syringe 30 is deployed and to immediately relieve the line pressure within the lumen 40 when the force applied to the syringe plunger 34 is removed.

Figure 5:
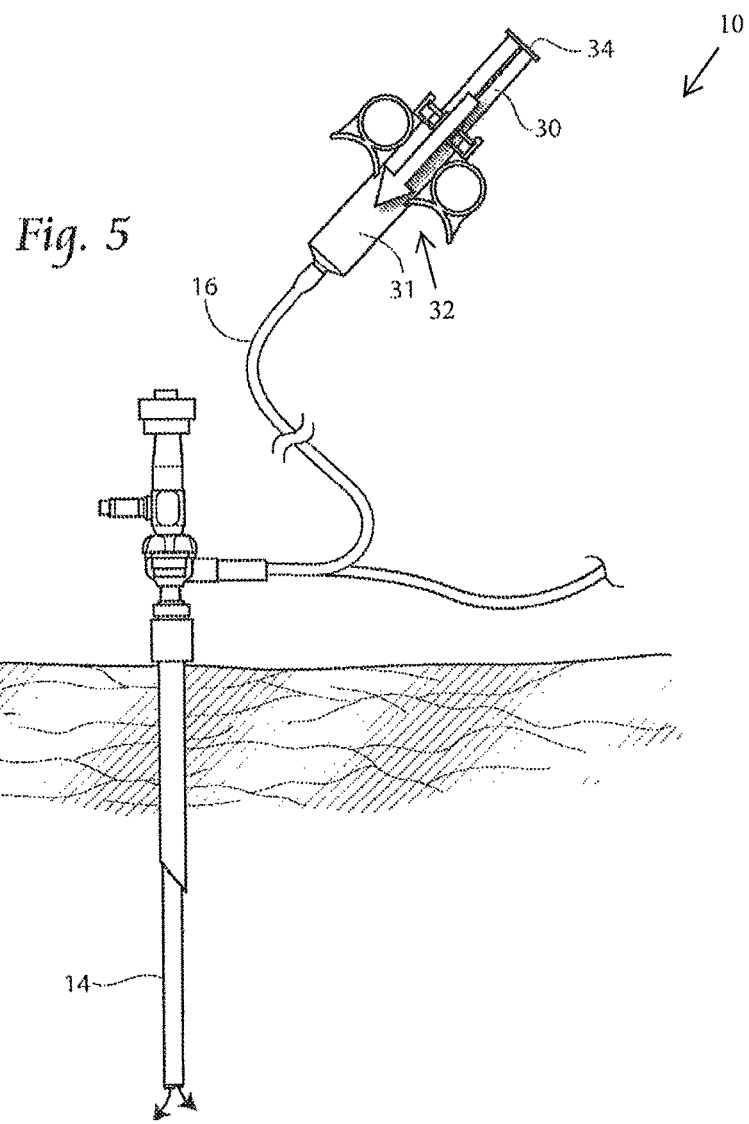
FIG. 5 is schematic view of the fluid dispensing control assembly demonstrating the delivery of fluid from the syringe.
Figure 6:
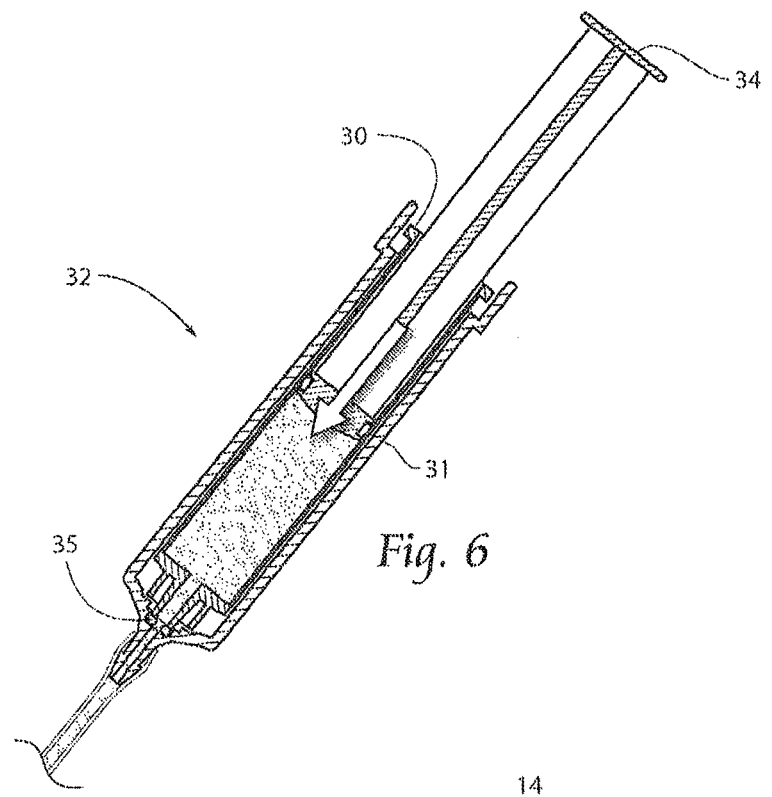
FIG. 6 depicts the application of pressure on a syringe plunger to begin the flow of fluid.
Figure 7:
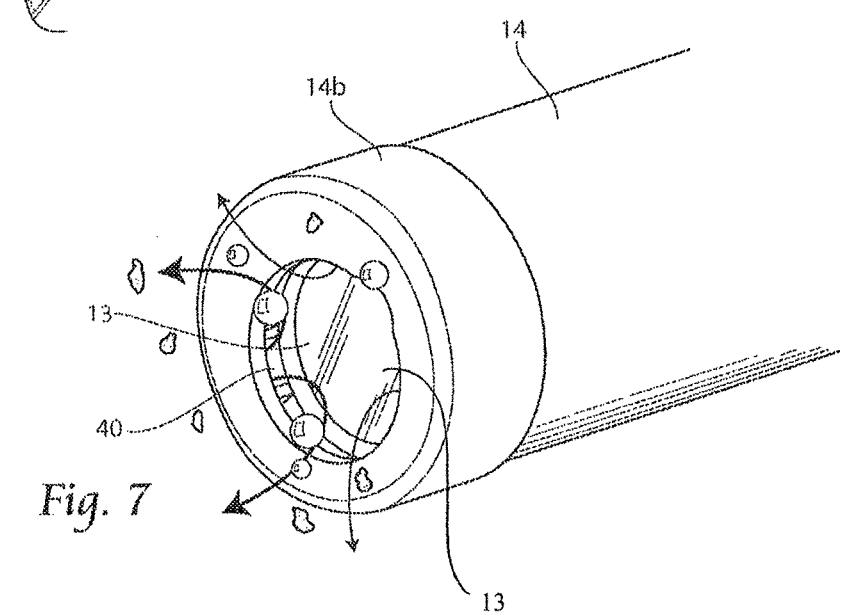
FIG. 7 depicts the distal end of a sheath with bursts of gas or liquid fluid clearing debris off of the scope lens.

FIGS. 4-6 depict the insertion of the syringe 30 into the syringe mating mechanism 31. This is accomplished by using the force applied to the syringe plunger 34 by the user to seat the tip 75 of the syringe 30 against the gasket 35 in the syringe mating mechanism 31. That is, when a force is applied to the plunger 34 of the syringe 30, that force is transferred through the fluid within the syringe barrel 71 to the distal end of the syringe barrel 71, forcing the tip 75 of the syringe 30 distally into the gasket 35 of the syringe mating mechanism 31. By doing so, the gasket 35 acts as a seal, and fluid can be delivered through the lumen 40. Further, in some embodiments, delivery of fluid from the syringe 30 through the syringe mating mechanism 31 and the lumen 40 can provide the minimum pressure required to open the valve 42 at the distal end of the lumen 40. Referring to FIG. 7, delivery of fluid from the syringe 30 through the syringe mating mechanism 31 can allow fluid to flow over the lens 13 of a laparoscope within the sheath 14 to remove debris.

FIGS. 8-10 show the removal of pressure from the syringe plunger 34. When the plunger 34 force is removed, the hermetic seal between the syringe 30 and the syringe mating mechanism 31 provided by the gasket 35 is lost. Further, the elastomeric gasket 35 acts as a spring to push the syringe 30 away and open the lumen 40 to atmospheric pressure, as depicted in FIGS. 8 and 10. That is, the shape of the gasket 35 can change temporarily as the syringe 30 is seated against the gasket. When pressure is removed from the plunger 34, the valve material can return to its original shape, thereby pushing the syringe away when the pressure on the plunger 34 is relieved. In this way, the line pressure in lumen 40 is immediately relieved. In the embodiments having grooves on the inner diameter of the barrel 61, fluid can escape therethrough when the plunger 34 is released, thereby allowing for faster pressure relief. Further, in embodiments having the valve 42, the release of pressure in the lumen 40 can thus cause the valve 42 to immediately close, thereby preventing the flow of fluid through the lumen 40, as depicted in FIG. 9.

The valve 42 can be configured to hold a column of fluid within the lumen 40 without opening. The fluid can thus remain in the lumen 40 between cleanings of the lens 13. As a result, when pressure is applied to the plunger of the syringe and fluid is ejected through the syringe, the fluid can immediately (i.e. with substantially no delay) exit the lumen 40 to flow over the lens 13. Further, in some embodiments, gas on a distal side of the valve 42, such as gas from the additional lumen(s) and gas within the patient's abdomen in use, can created a pressurized area on a distal side of the valve (i.e. a higher pressure than on the proximal side of the valve when the lumen 40 is open to the atmosphere). This difference in pressure can help keep fluid in the lumen 40 from weeping out. Finally, the valve 42 can be configured to withstand low pressure that may occur on the distal side of the valve 42 due to formation of a vortex of air from gas flowing through the additional lumen(s) 41.

In this way, fluid, such as surfactant cleaning fluid, is dispensed when the fluid source 30 is "on," wherein fluid is being provided through lumen 40, such as when syringe 30 plunger is depressed and the valve 42 is open. In contrast, fluid is not dispensed when the fluid source 30 is "off," wherein the syringe plunger is released and the one-way valve closes. The valve 42 and/or the syringe mating mechanism 31 thus prevent the uncontrolled dispensing of cleaning fluid by occluding the distal end of the lumen and isolating the lumen from gas flow through other lumens 41, advantageously avoiding the formation of bubbles and improving visualization through the lens 13 of the laparoscope.

Thus, the fluid dispensing control assembly 10 can be useful while performing intra-operative defogging, surgical debris deflection, and cleaning of a laparoscope lens during minimally invasive surgery without removing the laparoscope from the patient.

The foregoing is considered as illustrative only of the principles of the invention. Furthermore, since numerous modifications and changes will readily occur to those skilled in the art, it is not desired to limit the invention to the exact construction and operation shown and described. As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A view optimizing assembly for use in combination with a laparoscope, the assembly comprising:
    a sheath configured to be mounted over a shaft of a laparoscope, the sheath including at least one lumen extending within a wall of the sheath from a proximal end of the sheath to a distal end of the sheath, wherein the at least one lumen is configured to hold a fluid therein;
    a valve at a distal end of the at least one lumen, the valve configured to prevent release of fluid from the at least one lumen when closed and to allow the release of fluid from the at least one lumen when open; and
    a syringe mating mechanism at a proximal end of the least one lumen, wherein the syringe mating mechanism includes a gasket at a distal end thereof, wherein the gasket is configured such that, when a syringe is placed within the syringe mating mechanism and a pressure is placed on a plunger of the syringe, a distal end of the syringe seats within the gasket to allow fluid to flow into the at least one lumen;
    wherein the valve is configured to open when fluid is supplied to the at least one lumen from a syringe that is mated with the syringe mating mechanism and to close when a flow of fluid from the syringe stops; and
    wherein, when the pressure is released from the plunger of the syringe, the gasket is configured to act as a spring to push the syringe proximally to disengage the syringe from the syringe mating mechanism.

2. The view optimizing assembly of claim 1, wherein the valve is an elastomeric valve.

3. The view optimizing assembly of claim 1, wherein the valve is configured to open to allow the release of fluid when a predetermined minimum pressure is placed on the valve by the fluid.

4. The view optimizing assembly of claim 3, wherein the predetermined minimum pressure is approximately 20 mmHg.

5. The view optimizing assembly of claim 1, wherein the valve is configured to close when a pressure below a predetermined maximum pressure is placed on the valve by the fluid.

6. The view optimizing assembly of claim 5, wherein the predetermined maximum pressure is approximately 15 mmHg.

7. The view optimizing assembly of claim 1, wherein the gasket is configured to seal the syringe within the syringe mating mechanism when the distal end of the syringe seats within the gasket.

8. The view optimizing assembly of claim 1, wherein the gasket is an elastomeric gasket.

9. The view optimizing assembly of claim 1, wherein at least one additional lumen is configured to convey gas from the proximal end of the sheath to the distal end of the sheath.

10. The view optimizing assembly of claim 1, wherein the valve is a one-way valve.

11. A view optimizing assembly for use in combination with a laparoscope, the assembly comprising:
    a sheath configured to be mounted over a shaft of a laparoscope, the sheath including a lumen extending from a proximal end of the sheath to a distal end of the sheath, wherein the lumen is configured to hold a fluid therein; and
    a syringe mating mechanism fluidically connected to the lumen, the syringe mating mechanism including a barrel with a tapered distal end, a plurality of finger grips extending from the barrel, and a gasket positioned within the tapered distal end, wherein the gasket is configured such that, when a syringe is placed within the syringe mating mechanism and a user pressure is placed on a plunger of the syringe, a distal end of the syringe seats within the gasket to allow fluid to flow into the lumen from the syringe; and
    wherein, when the pressure is released from the plunger of the syringe, the gasket is configured to act as a spring to push the syringe proximally to disengage the syringe from the syringe mating mechanism.

12. The view optimizing assembly of claim 11, wherein the gasket is configured to seal the syringe within the syringe mating mechanism when the distal end of the syringe seats within the gasket.

13. The view optimizing assembly of claim 11, wherein the gasket is an elastomeric gasket.

14. A view optimizing assembly for use in combination with a laparoscope, the assembly comprising:
    a sheath configured to be mounted over a shaft of a laparoscope, the sheath including at least one lumen extending within a wall of the sheath from a proximal end of the sheath to a distal end of the sheath, wherein the at least one lumen is configured to hold a fluid therein;
    a valve at a distal end of the at least one lumen, the valve configured to hold a column of fluid within the at least one lumen without opening, the valve further configured to allow release of the column of fluid from the at least one lumen when a predetermined minimum pressure is placed on the column of fluid; and
    a syringe mating mechanism at a proximal end of the at least one lumen, wherein the syringe mating mechanism includes a gasket at a distal end thereof, wherein the gasket is configured such that, when a syringe is placed within the syringe mating mechanism and a pressure is placed on a plunger of the syringe, a distal end of the syringe seats within the gasket to allow fluid to flow into the at least one lumen; and wherein, when the pressure is released from the plunger of the syringe, the gasket is configured to act as a spring to push the syringe proximally to disengage the syringe from the syringe mating mechanism.

15. The view optimizing assembly of claim 14, wherein the predetermined minimum pressure is approximately 20 mmHg.

16. The view optimizing assembly of claim 14, wherein the predetermined minimum pressure is approximately 15 mmHg.

17. The view optimizing assembly of claim 14, wherein at least one additional lumen is configured to convey gas from the proximal end of the sheath to the distal end of the sheath.

\* \* \* \* \*